(12) United States Patent
Westhoff et al.

(10) Patent No.: US 12,337,121 B2
(45) Date of Patent: Jun. 24, 2025

(54) CATHETER SHAFT AND CATHETER AND METHOD FOR THE PRODUCTION THEREOF

(71) Applicant: BIOTRONIK AG, Buelach (CH)

(72) Inventors: Felix Westhoff, Meilen (CH); Tobias Schaefer, Blumberg-Fuetzen (DE)

(73) Assignee: BIOTRONIK AG, Buelach (CH)

( * ) Notice: Subject to any disclaimer, the term of this patent is extended or adjusted under 35 U.S.C. 154(b) by 1126 days.

(21) Appl. No.: 16/942,459

(22) Filed: Jul. 29, 2020

(65) Prior Publication Data

US 2020/0353209 A1    Nov. 12, 2020

Related U.S. Application Data

(63) Continuation-in-part of application No. 14/810,806, filed on Jul. 28, 2015, now abandoned.

(30) Foreign Application Priority Data

Aug. 14, 2014    (DE) .......................... 102014011948.3

(51) Int. Cl.
  *A61M 25/00*    (2006.01)
  *A61M 25/09*    (2006.01)
  *B29C 65/00*    (2006.01)

(52) U.S. Cl.
  CPC .... *A61M 25/0026* (2013.01); *A61M 25/0014* (2013.01); *A61M 25/0097* (2013.01);
  (Continued)

(58) Field of Classification Search
  CPC .. A61M 2025/0039; A61M 2025/0034; A61M 2025/0059; A61M 2025/0098;
  (Continued)

(56) References Cited

U.S. PATENT DOCUMENTS 4,961,809 A * 10/1990 Martin ................ A61M 25/003
                                                156/322
5,478,331 A    12/1995 Heflin et al.
(Continued)

FOREIGN PATENT DOCUMENTS

EP        0227230       7/1987
WO       199841277      9/1998

OTHER PUBLICATIONS

European Search report from the corresponding European Patent Application No. 15170754, mailed Jan. 8, 2016. **reference provided to USPTO with the Jan. 12, 2016 IDS filing in parent U.S. Appl. No. 14/810,806.

*Primary Examiner* — Kevin C Sirmons
*Assistant Examiner* — Alexandra Lalonde
(74) *Attorney, Agent, or Firm* — Greer, Burns & Crain, Ltd.; Steven P. Fallon (57) ABSTRACT

A catheter having a catheter shaft connected to a two-part connecting piece. The catheter shaft includes a first tube forming an inflation lumen and a second tube disposed at least partially within the first tube to form a second lumen. The first tube and the second tube terminate proximally at a same longitudinal position. An outer surface of the second tube is welded longitudinally to an inner surface of the first tube to form a weld seam. The connecting piece includes a channel through a body of the connecting piece extending to and in fluid communication with the inflation lumen and a conical-shaped proximal section or element with a conical-shaped outer contour that fits into a distal element so that the second lumen seals around the proximal element and sole access to a proximal end of the inflation lumen is through the distal element.

11 Claims, 10 Drawing Sheets

(52) U.S. Cl.
CPC ....... *A61M 25/09* (2013.01); *B29C 66/52271* (2013.01); *B29C 66/712* (2013.01); *A61M 2025/0034* (2013.01); *A61M 2025/0059* (2013.01)

(58) Field of Classification Search
CPC .. A61M 2025/0037; A61M 2025/0004; A61M 25/0026; A61M 25/0028; A61M 25/0009; A61M 25/0014; A61M 25/0097; A61M 25/09; A61M 25/0029; A61M 25/0032; A61M 25/00; A61M 2025/0006; A61M 2025/0031; A61M 2025/004; A61M 2025/0042; A61M 25/0021; A61M 25/0023; A61M 39/105; B29C 66/52271; B29C 66/712; B29C 66/52272; B29C 66/5227

See application file for complete search history.

(56) References Cited

U.S. PATENT DOCUMENTS

| | | | | |
|---|---|---|---|---|
| 5,514,073 | A | 5/1996 | Miyata et al. | |
| 5,833,672 | A | 11/1998 | Kawata et al. | |
| 5,976,103 | A * | 11/1999 | Martin | A61M 25/0026 604/35 |
| 6,248,092 | B1 | 6/2001 | Miraki et al. | |
| 6,273,404 | B1 * | 8/2001 | Holman | A61M 25/0097 604/525 |
| 6,585,687 | B1 | 7/2003 | Shkolnik | |
| 2003/0158539 | A1 * | 8/2003 | Bouphavichith | A61M 39/10 604/533 |
| 2003/0163082 | A1 * | 8/2003 | Mertens | A61M 1/3659 604/43 |
| 2003/0220628 | A1 | 11/2003 | Klisch et al. | |
| 2004/0004311 | A1 | 1/2004 | Mertens et al. | |
| 2005/0059958 | A1 | 3/2005 | Lessard et al. | |
| 2005/0131445 | A1 | 6/2005 | Holman et al. | |
| 2005/0277878 | A1 * | 12/2005 | Lee | A61M 25/1036 604/103 |
| 2007/0078439 | A1 | 4/2007 | Grandt et al. | |
| 2008/0004568 | A1 * | 1/2008 | Jeffrey | A61M 25/1006 604/96.01 |
| 2008/0214991 | A1 * | 9/2008 | Haarala | A61M 25/0026 604/43 |
| 2010/0268183 | A1 | 10/2010 | Rowe et al. | |

* cited by examiner

CATHETER SHAFT AND CATHETER AND METHOD FOR THE PRODUCTION THEREOF

PRIORITY CLAIM AND CROSS REFERENCE TO RELATED APPLICATIONS

This application is a continuation-in-part of and claims priority under 35 U.S.C. § 120 from pending U.S. application Ser. No. 14/810,806, filed Jul. 28, 2015, which application is incorporated by reference herein and claims benefit of priority under 35 U.S.C. § 119 and applicable treaties from German patent application serial no DE 10 2014 011 948.3, filed Aug. 14, 2014; the entire content of which is herein incorporated by reference in its entirety.

TECHNICAL FIELD

The invention relates to a catheter shaft, a catheter and a method for the production of such a catheter shaft or catheter.

BACKGROUND OF THE INVENTION

Catheters have small tubes or sleeves with different diameters, in the region of the shaft thereof, which small tubes or sleeves can be inserted into the particular body cavity to be treated. So-called balloon catheters are used primarily in angioplasty to expand or reopen a vessel (percutaneous transluminal coronary angioplasty—PTCA, also percutaneous coronary intervention—PCI). Such a balloon catheter has a shaft, which has an initially non-dilated balloon in a predetermined region. To perform treatment, a guide wire is first inserted into the vessel to be treated. Next, the shaft of the balloon catheter is advanced along the guide wire to the site of the vessel to be treated, thereby placing the balloon in the region of the site of the vessel to be treated, where a stenosis is located, for instance. The balloon is then dilated, i.e. unfolded and/or expanded, thereby reopening or expanding the site to be treated. Finally, the balloon is deflated and removed from the vessel along the guide wire. The guide wire is also withdrawn from the vessel at the same time or subsequent thereto. Balloon catheters of that type can also be used to apply intraluminal endoprostheses at a site to be treated in a body cavity.

Such a catheter typically includes, in addition to the shaft thereof, a connecting piece on the proximal end thereof, which is used to connect the catheter to the catheter control and, optionally, to the fluid supply. The connecting piece is connected to the catheter shaft. The distal end of the catheter shaft is also referred to as the catheter tip.

Catheters having several, in particular, two lumens are used in particular for the application in angioplasty, wherein, e.g., the first lumen is used to accommodate the guide wire and the second lumen is used for the passage of a fluid or a gas. For catheters that are used in hemolysis, the first lumen can be used to withdraw blood from the body of the patient and the second lumen can be used to return the purified blood. Such a multi-lumen catheter is described in WO 98/41277 A1.

As is also found in document WO 98/41277 A1, when the shaft has two lumens, a basic distinction is made between two types of shafts. In a so-called two-lumen tube, the first lumen and the second lumen are arranged next to one another, separated only by a partition wall. In the coaxial shaft design, two cylindrical lumens are provided in hollow cylindrical elements, wherein the smaller hollow-cylindrical element (inner tube) is arranged within the lumen of the larger hollow cylinder (outer tube). Document U.S. Pat. No. 6,248,092 B1 shows a coaxial shaft design.

In the case of a two-lumen tube, for the application in PTCA, an inner tube for the balloon segment must be installed on the shaft and, in many cases, a guide wire lumen extension as well, in order to enable the guide wire to pass through the entire catheter (from the connecting piece up to the catheter tip).

The two-lumen design also has the disadvantage that, in the region in which the extension is mounted on the shaft, relatively small constrictions and hardening of the guide wire lumen occur, which can affect the push- and trackability. In addition, there is a risk of a leak in the region. Since the material properties of the shaft must meet all the requirements of the system, it is often only possible to reach a compromise between bursting strength, guidewire friction, and flexibility.

The conventional coaxial shaft design is disadvantageously characterized in that the diameter of the shaft profile is relatively large. In addition, the push-properties at the catheter tip worsen, due to the design.

The conventional coaxial design has the further disadvantage that the deflation time is greater, due to greater fluid friction, as compared to the two-lumen design, given the same dimensions. In addition, since there is no connection of inner tube and outer tube along a large portion of the shaft, relative movements of the cylindrical elements, which are nested inside one another, can occur under load, which can negatively influence the tracking and pushing properties of the catheter.

The problem is therefore that of improving the above-mentioned properties of the catheter and providing a cost-effective method for producing such a catheter.

SUMMARY OF THE INVENTION

A preferred embodiment provides a catheter having a catheter shaft connected to a two-part connecting piece. The catheter shaft includes a first tube forming a first lumen and a second tube disposed at least partially within the first tube to form a second lumen. The first and second tubes terminate proximally at a same longitudinal position. An outer surface of the second tube is welded longitudinally to an inner surface of the first tube to form a weld seam. The connecting piece includes a conical-shaped proximal element with a conical-shaped outer contour that fits into a distal element so that the second lumen seals around the proximal element and sole access to a proximal end of the first lumen is through the distal element.

DETAILED DESCRIPTION OF THE PREFERRED EMBODIMENTS

Problems mentioned in the backgrounds are solved by a preferred catheter shaft having a first tube, which forms a first lumen, and a second tube, which forms a second lumen and is arranged at least partially within the first tube. The second tube is welded, via the outer surface (circumferential surface) thereof, to the inner surface of the first tube, at least in sections. Therefore, the inner diameter of the first tube must be larger than the outer diameter of the second tube. The outer diameter of the second tube and the inner diameter of the first tube preferably form a ratio that is between 0.4 and 0.95, particularly preferably between 0.6 and 0.9. That is, the outer diameter of the second, inner tube is at least 0.4-fold, preferably 0.6-fold the inner diameter of the first, outer tube and, at most, 0.95-fold, preferably 0.9-fold the inner diameter of the first, outer tube.

The (inner) lumen of the first tube is preferably the inflation lumen, while the (inner) lumen of the second tube, i.e., the smaller lumen, is preferably the guide wire lumen.

Assembly of the system is simplified by such a design of a catheter shaft, and so the costs to produce a catheter are reduced and less waste is produced. In addition, the accessibility by a guide wire is improved due to the use of two tubes, which are arranged inside one another and are fastened to one another, since the guide wire lumen is designed so as to be completely homogeneous and round. The deflation time can be reduced and greater push can be achieved as compared to the conventional coaxial shaft design without a connection of inner tube and outer tube.

In the catheter shaft, the first tube and the second tube are arranged inside one another such that the longitudinal axes of the tubes, each of which preferably has a circular cross section, extend parallel to one another. Cross-sectional shapes other than the circular shape are also conceivable for the first tube and/or the second tube (e.g., a rectangular cross section).

In a particularly preferred embodiment, the weld seam extends parallel to the longitudinal axis of the first tube and/or the second tube. Constrictions in the region of the shaft are prevented as a result, thereby also improving the push- and trackability properties.

It is furthermore advantageous when the first tube has a laser-active material at least in the region of the inner surface thereof and/or the second tube has a laser-active material at least in the region of the outer surface thereof (e.g., on the circumferential surface thereof). Such a laser-active material heats up when irradiated with a laser having a certain wavelength. The first and the second tube can then be easily welded at these regions having laser-active material, thereby further simplifying the assembly of the system. The wavelength of the laser that is used depends on the material and is preferably selected accordingly. In addition, the first tube and the second tube can be connected such that the surface of the tubes is not deformed, which can negatively affect the properties of the catheter shaft.

Non-laser-active materials can be connected by thermal radiation (e.g., heat-sealing jaws, hot air, or laser).

The catheter shaft can be further improved in that the first tube has a first chemical composition and the second tube has a second chemical composition, wherein the second chemical composition is different from the first chemical composition. In an advantageous embodiment of the invention, the second tube is made from a polyamide, for example PA12. Polyamide ensures low friction between the guide wire and the tube. In this embodiment, the first tube is advantageously made from a thermoplastic copolyamide, for example PEBAX, whereby high flexibility of the catheter system is achieved overall. By this solution according to the invention, the materials of the tubes can be optimized for the particular application according to the particular requirements (e.g., with respect to bursting pressure, flexibility, coating, guide wire friction) and, therefore, the properties of the whole system are also improved.

Advantageously, the first and/or the second tube are/is made from at least one material selected from the group containing polyamides, in particular PA12, thermoplastic elastomers, in particular thermoplastic copolyamides such as PEBAX 7033, PEBAX 7233, GRILAMID L25 and VESTAMID L2101.

The above-described problem is further solved by a catheter including a catheter shaft having the aforementioned new features. As a result, the catheter according to the invention has the aforementioned advantages.

In a particularly preferred embodiment, the shaft of the catheter is connected to a connecting piece, which has at least one conical section, on which the proximal end of the first tube or the second tube is arranged. The cone is created such that the outer cross section of the section increases in the proximal direction. In addition, the conical section preferably has an inner, continuous opening. The advantage of this solution is that the shaft tube is automatically proximally sealed when inserted onto the connecting piece. As a result, the assembly of the catheter can be further simplified and a particularly good seal can be achieved in the region of the connecting piece. The conical section is preferably arranged within a substantially hollow cylindrical body of the connecting piece, at the proximal end thereof.

The purpose of the cone is to widen the lumen of the guide wire when the tube of the guide wire is arranged on the conical section of the connecting piece. In addition to the tight seal, a gentle transition from the shaft tube to the connecting piece is achieved, thereby preventing an edge on which the guide wire could get stuck.

In another preferred embodiment, the connecting piece can have a multi-piece design, namely having at least one distal element and a proximal element having the conical section, wherein the distal element and the proximal element can be connected to one another, preferably by a snap-in connection, a welded connection, or another preferably non-detachable connection. A secure fastening of the catheter shaft can be achieved by the multi-piece design of the connecting piece, thereby making it possible to omit a bonding is with the catheter shaft. In addition, the distal element can have an anti-kink device on the distal end thereof. This is preferably formed from annular elements, which are connected to one another by webs extending in the longitudinal direction (axial direction). The anti-kink device is dimensioned such that this externally surrounds the first tube of the catheter shaft after installation of the connecting piece.

In a preferred embodiment of the design as a multi-piece connecting piece, the distal element is produced using a two-component injection-molding process. The anti-kink device is made from a material that is softer and more elastic than the rest of the distal element. Due to the use of a softer material, the kink protection is more efficient and can be sealed better using optional seals made from the same material. The retention force of the catheter tubes on the connecting piece is thereby also increased. The use of different materials can also be advantageous for the proximal element. If a softer and more elastic material is used for the conical, distal end of the proximal element, the seal integrity is improved and spring action is achieved via the elastic properties. This spring action maintains the pressure for a long period of time in the case of a snap-in connection.

The softer material for the anti-kink device is preferably a polyether block amide (PEBA or TPE-A, which is available, for example, under the trade names PEBAX, VESTAMID E, GRILFLEX), a thermoplastic elastomer (TPE), in particular a polyester elastomer (TPE-E, e.g., available under the trade name HYDREL) The other material for the remaining elements of the connecting piece is preferably an amorphous polyamide (e.g., available under the trade names GRILAMID TR, TROGAMID), a polycarbonate (PC) (e.g., available under the name MAKROLON) or a polyethylene terephthalate (PET).

Particularly preferably, in particular with the single-piece embodiment of the connecting piece, the connecting piece can be additionally bonded on the inner side of the distal end thereof to the outer surface of the first tube, thereby preventing the respective tube arranged on the conical section of the connecting piece from slipping off of the cone.

The above-described solutions having the conical section of the connecting piece also is make it possible to effectively automate the process of joining the shaft and the connecting piece.

For the case in which the inflation lumen (e.g., the first tube having a lumen for a fluid, not for the guide wire) is simultaneously closed by the expansion of the guide wire lumen (e.g., second tube), an additional incision on the inflation lumen can provide assistance. This incision could take place, e.g., directly when the connecting piece is connected to the proximal end of the shaft. A plastic blade, which makes the incision, is provided for this purpose in the inflation lumen. The plastic blade is preferably arranged on the connecting piece on a groove or rib extending parallel to the longitudinal axis.

The aforementioned statement of the problem is furthermore solved by a method for producing a catheter shaft, which has the following steps:
providing a first tube and a second tube,
arranging the second tube at least partially in the first tube, and
welding the second tube, via the outer surface thereof, to the inner surface of the first tube, at least in sections.

The first tube and the second tube are thereby arranged inside one another such that the longitudinal axes of the two tubes, each of which preferably has a circular cross section, extend parallel to one another when finished. In addition, in a particularly preferred embodiment, the welding is carried out such that the weld seam extends parallel to the longitudinal axis of the first tube and/or the second tube.

The above-described method according to the invention can be carried out particularly easily and cost-effectively.

The aforementioned problem is furthermore solved by a method for producing a catheter, in which the aforementioned steps for producing a catheter shaft are carried out and then the additional step, in which the catheter shaft is connected at the proximal end thereof to a single-piece connecting piece or a multi-piece connecting piece having at least one distal element and one proximal element.

In a particularly preferred embodiment, the proximal end of the catheter shaft is inserted into the preferably hollow cylindrical body of the single-piece connecting piece. Particularly preferably, the first tube or the second tube are arranged over an above-described conical section of the connecting piece such that the tube is automatically sealed. The lumen of the corresponding tube is thereby widened in this region. After insertion and connection of the catheter shaft with the connecting piece, the connecting piece is preferably bonded at the inner side of the distal end of the body thereof to the outer surface of the first tube and/or the second tube.

As an alternative, when a multi-piece connecting piece is used, the proximal end of the catheter shaft is threaded into a continuous opening of the distal element, and then the proximal element is inserted, via the conical section thereof, into the proximal end of the catheter shaft, preferably into the proximal end of the second tube, and then the distal element is displaced in the proximal direction to the proximal element of the connecting piece and is connected thereto, e.g., by a snap-in connection. This is a particularly simple and cost-effective procedure for fastening the catheter shaft on the connecting piece. When the proximal end of the catheter shaft is threaded into the distal element, it is also threaded through a continuous opening of the anti-kink device.

Further objectives, features, advantages, and possible applications of the invention will become apparent from the following description of embodiments, with reference to the figures. All the features described and/or illustrated graphically here, either alone or in any combination, may form the subject matter of the present invention, even independently of how they are combined in the individual claims or how they refer back to previous claims.

Figure 1:
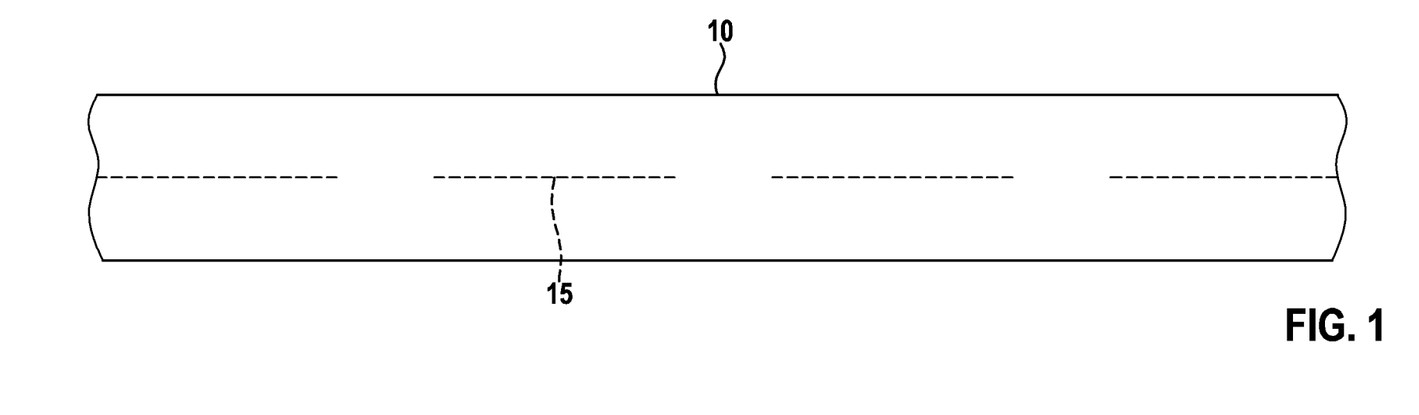
FIG. 1 shows a view from the side of a catheter shaft according to the invention.
Figure 2:
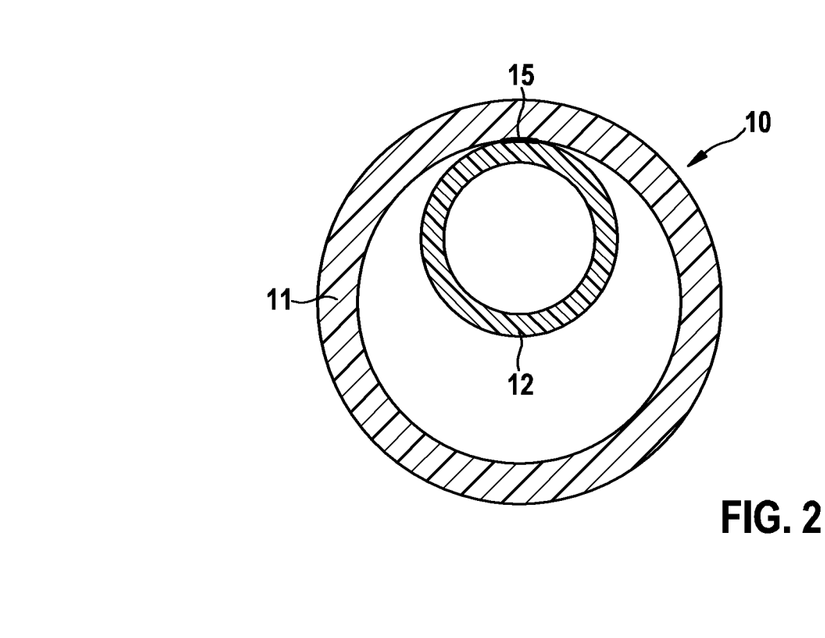
FIG. 2 shows a cross section of the catheter shaft according to the invention, from FIG. 1.

FIGS. 1 and 2 show a catheter shaft 10 having a first tube 11 and a second tube 12, wherein the first tube 11 and the second tube 12 are arranged inside one another parallel to the longitudinal axis thereof. In the region of the outer surface thereof (circumferential surface), the second tube 12 is welded to the first tube 11, i.e., in particular via the inner surface thereof, along a weld seam 15. The weld seam 15 extends parallel to the is longitudinal axis of the first tube 11 and the second tube 12, wherein the weld seam 15 extends either along the entire length of the catheter shaft or in sections, as shown in FIG. 1.

In order to obtain a good weld between the first tube 11 and the second tube 12, the first tube 11 is formed from a laser-active material in the region of the inner surface thereof and/or the second tube 12 is formed from a laser-active material in the region of the outer circumferential surface thereof. The first tube 11 can be made, e.g., from PEBAX, and the second tube 12 can be made, e.g., from polyamide 12 (PA12). The laser-active material is preferably applied on the circumferential surface of the second tube 12.

The second tube 12 can be used, e.g., for the placement of a guide wire while the first tube 11 is the inflation lumen.

Figure 3A:
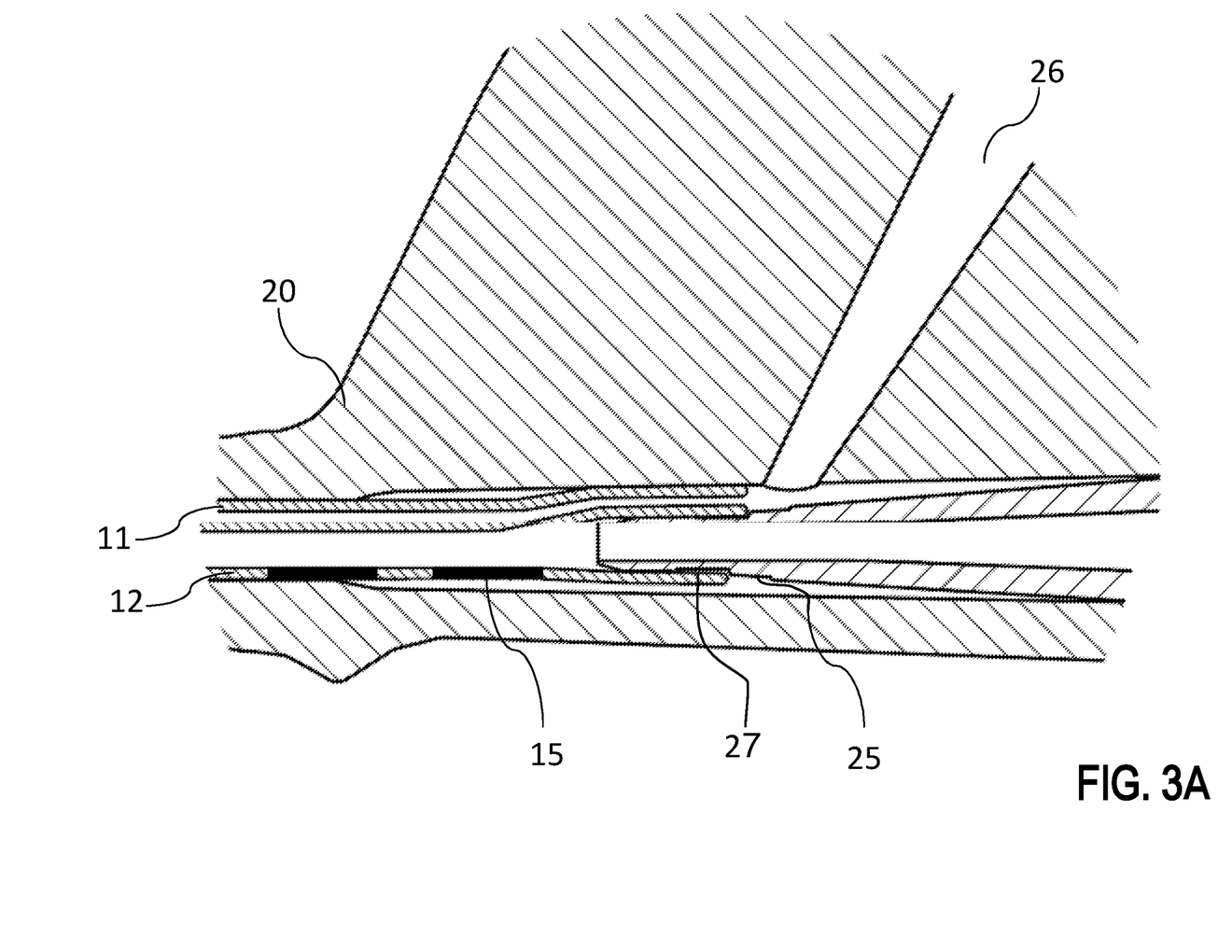
FIG. 3A shows a longitudinal section of a catheter according to the invention in the region of a first embodiment of a connecting piece.

The catheter according to the invention shown in FIG. 3A includes a connecting piece 20, which is connected to the proximal end of the catheter shaft 10. The body of the connecting piece 20 is hollow-cylindrical at the distal end (not shown) thereof, thereby enabling both the first tube 11 and the second tube 12 of the catheter shaft 10 to be inserted into the opening of the connecting piece 20. In addition, a conical section 25 is provided at the proximal end of the connecting piece 20, onto which the second tube 12 is slid, thereby automatically sealing this tube 12. Furthermore, the connecting piece 20 has a channel 26, into which the lumen of the first tube 11 leads, the channel connecting the tube to a fluid source for inflating/deflating a balloon. As shown in FIG. 3A, the first tube 11 and the second tube 12 terminate proximally at a same longitudinal position with respect to the catheter axis, or in other words the proximal ends of the first and second tubes terminate proximally along a same plane perpendicular to the catheter axis.

Figure 3B:
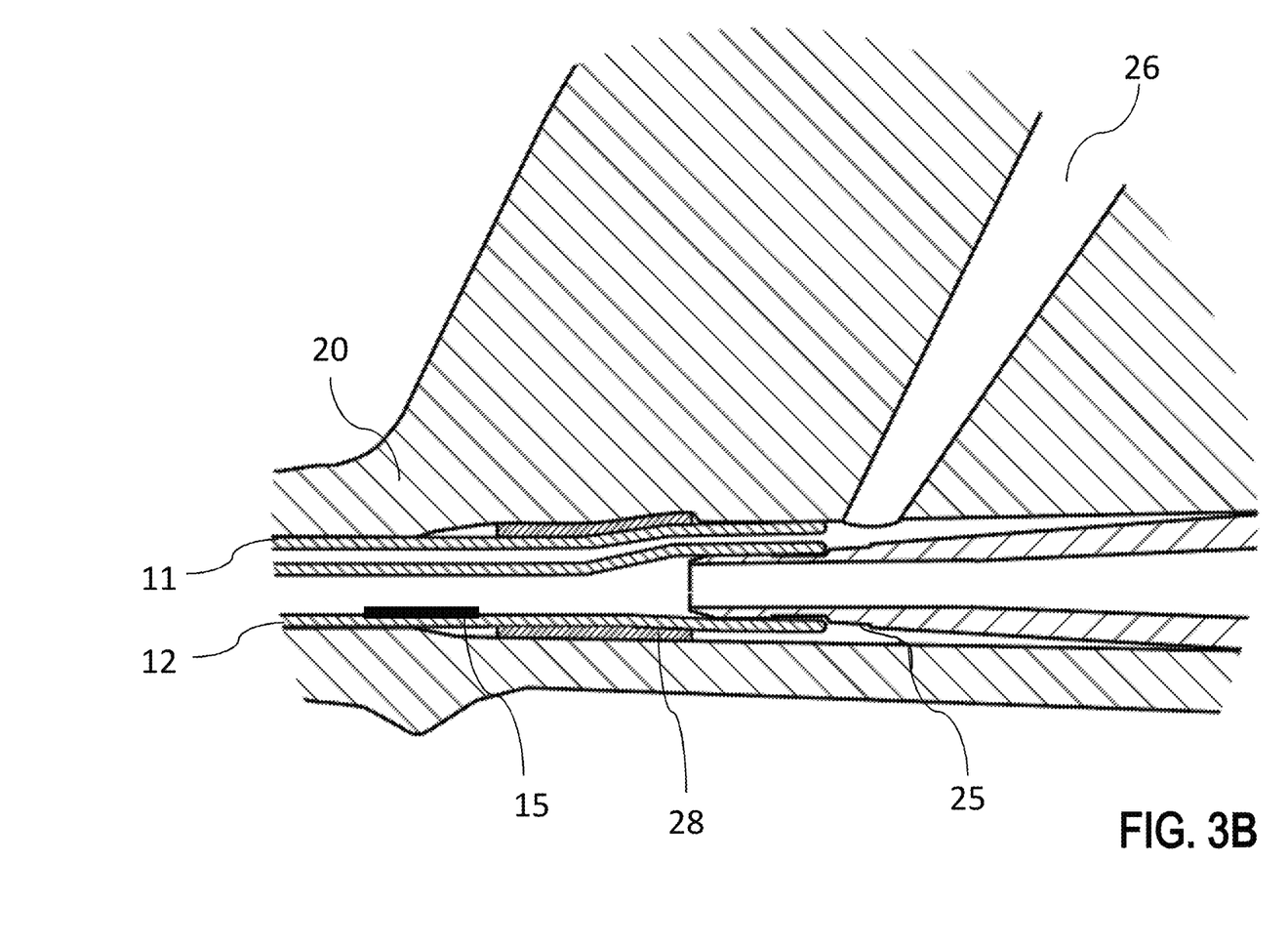
FIG. 3B shows a longitundinal section of a catheter according to the invention in the region of a second embodiment of a connecting piece.
Figure 4:
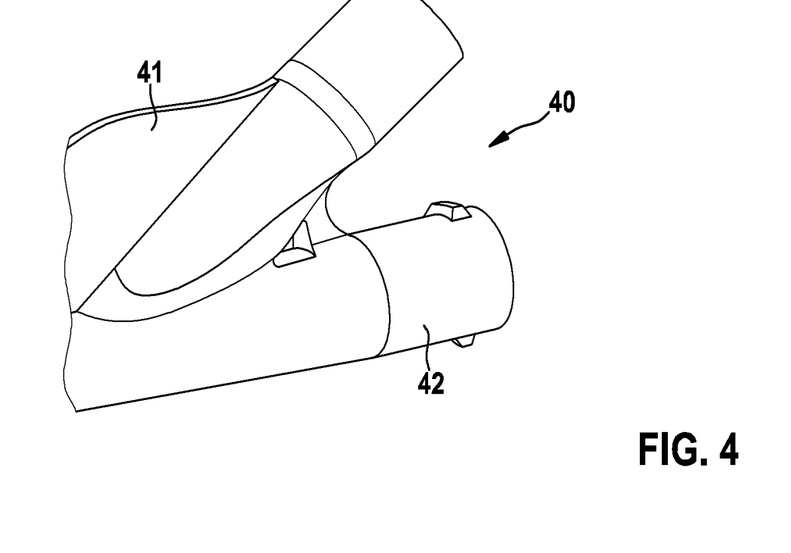
FIG. 4 shows a perspective view from the side of a second embodiment of a connecting piece for a catheter according to the invention having a distal element and a proximal element, which is connected to the distal element.
Figure 5:
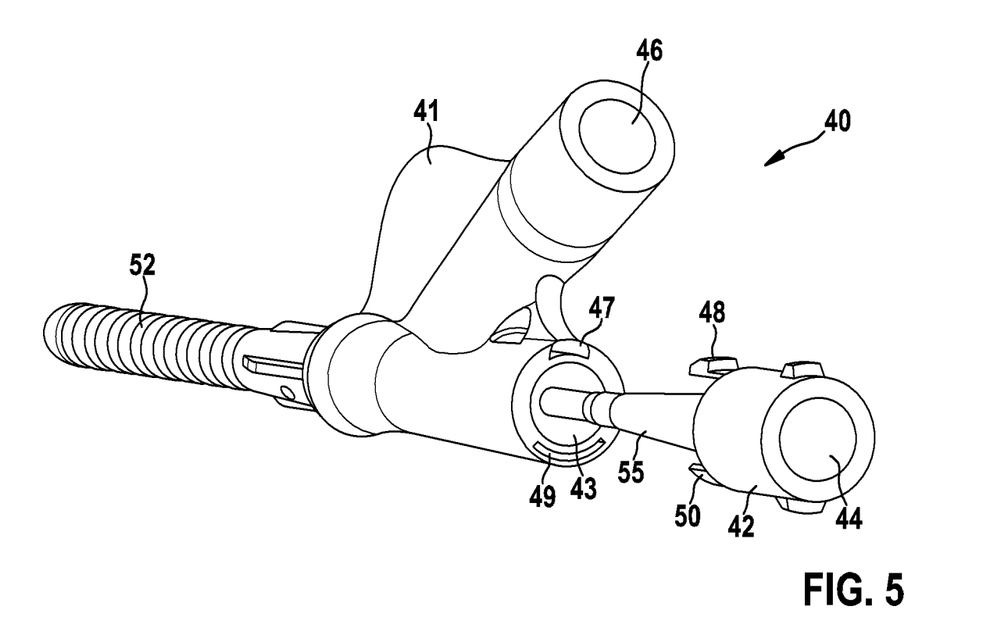
FIG. 5 shows a perspective view from behind of the embodiment of the connecting piece according to FIG. 4, wherein the distal element and the proximal element are shown separated.
Figure 6:
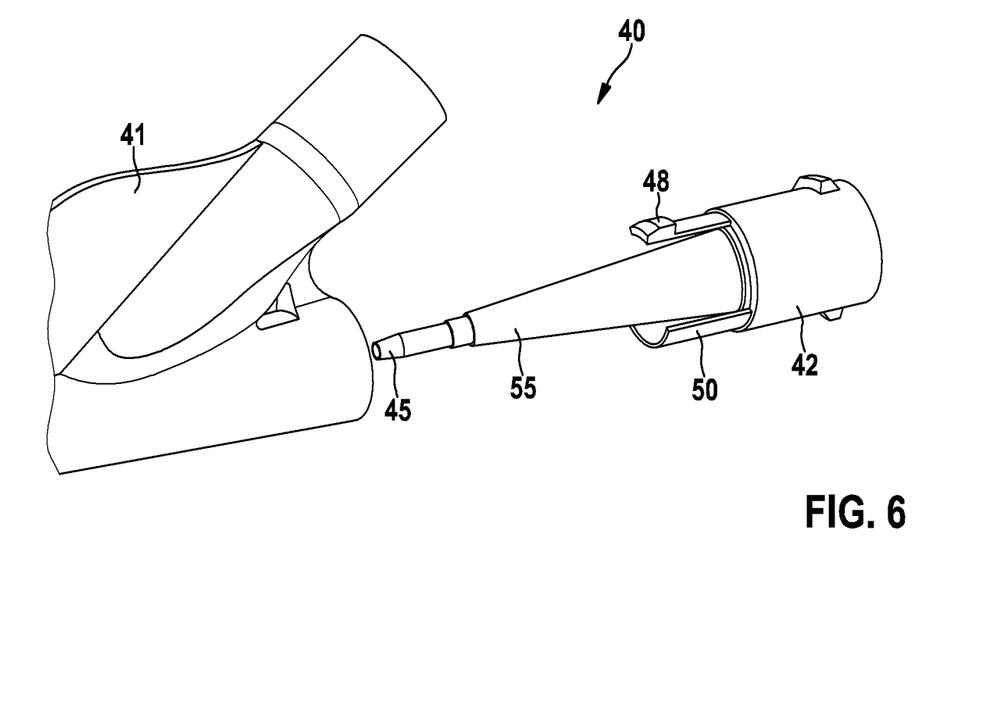
FIG. 6 shows a perspective view from the side of another separated illustration of the distal element and the proximal element of the embodiment of a connecting piece according to FIG. 4.
Figure 7:
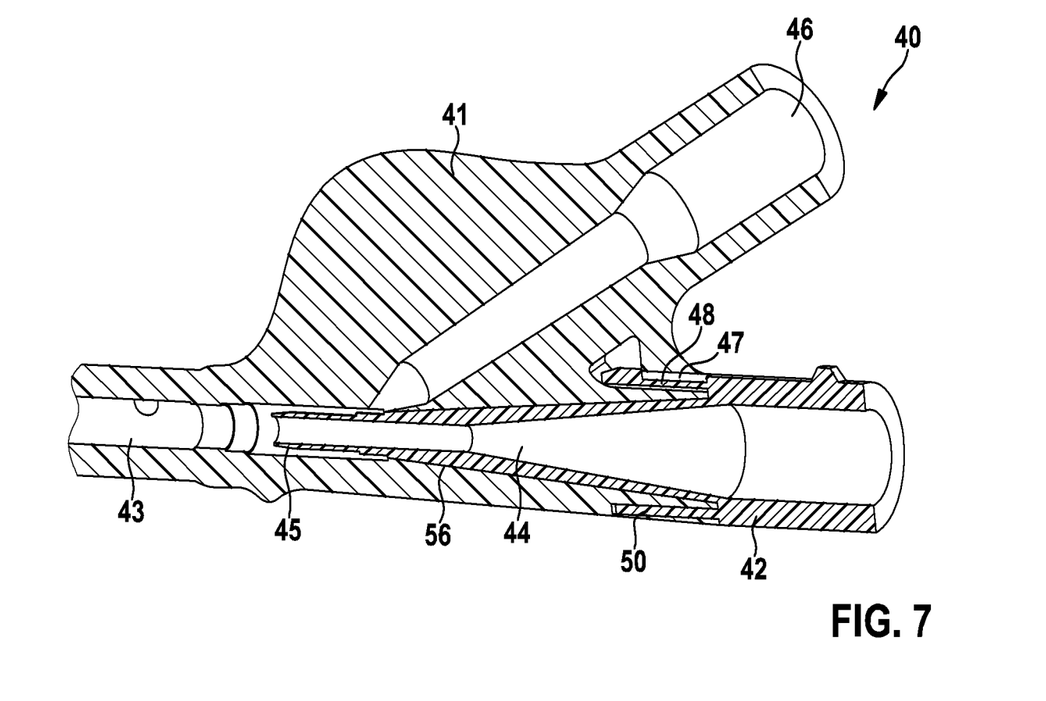
FIG. 7 shows a cross section of the embodiment of the connecting piece according to FIG. 4 with the distal element and the proximal element connected.
Figure 8:
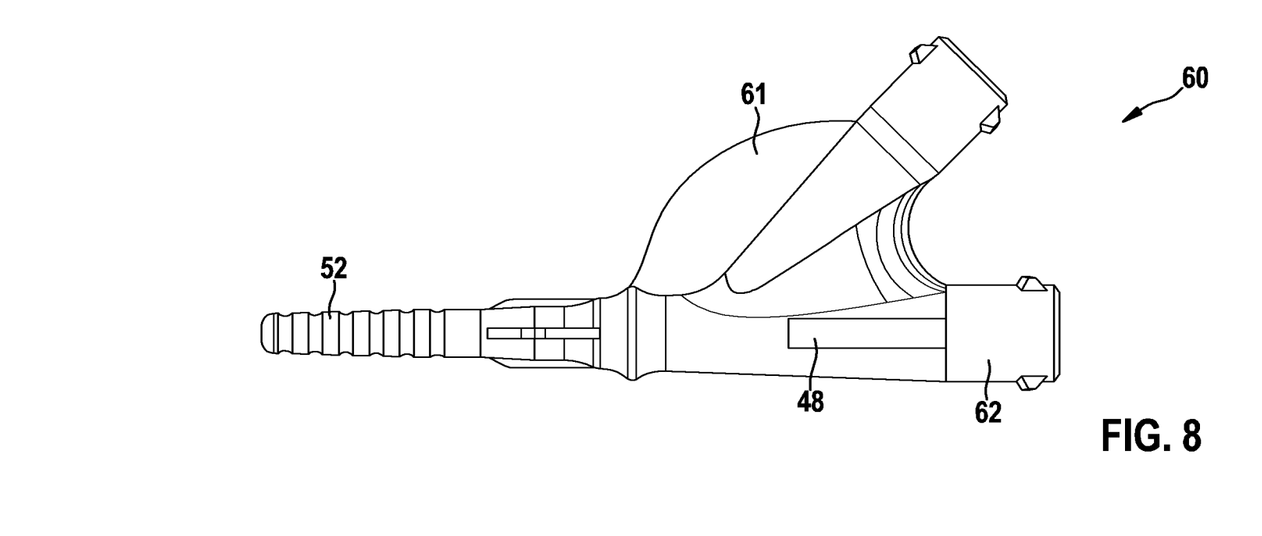
FIG. 8 shows a perspective view from the side of a third embodiment of a connecting piece for a catheter according to the invention having a distal element and a proximal element, which is connected to the distal element.
Figure 9:
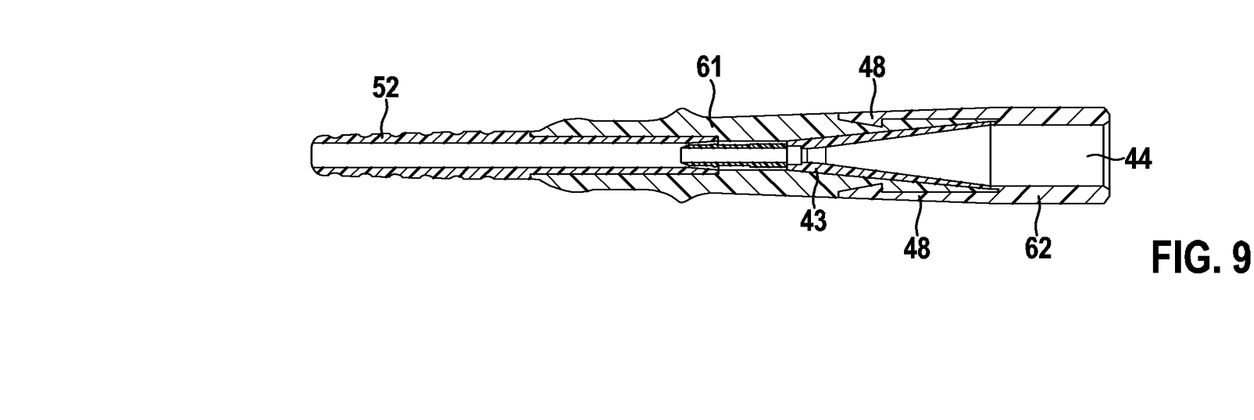
FIG. 9 shows a cross section of the embodiment of a connecting piece according to FIG. 8.
Figure 10:
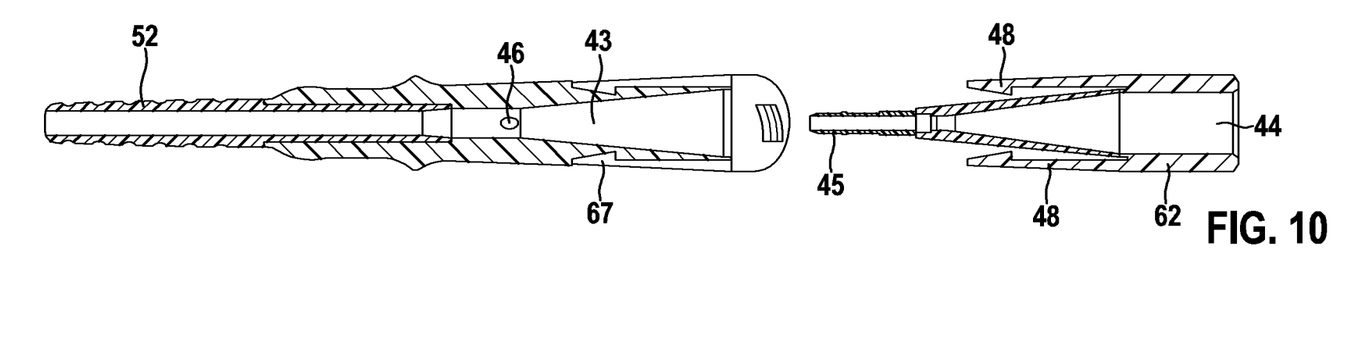
FIG. 10 shows the cross section according to FIG. 9 of the embodiment of a connecting piece according to FIG. 8, wherein the distal element and the proximal element are shown separately.
Figure 11:
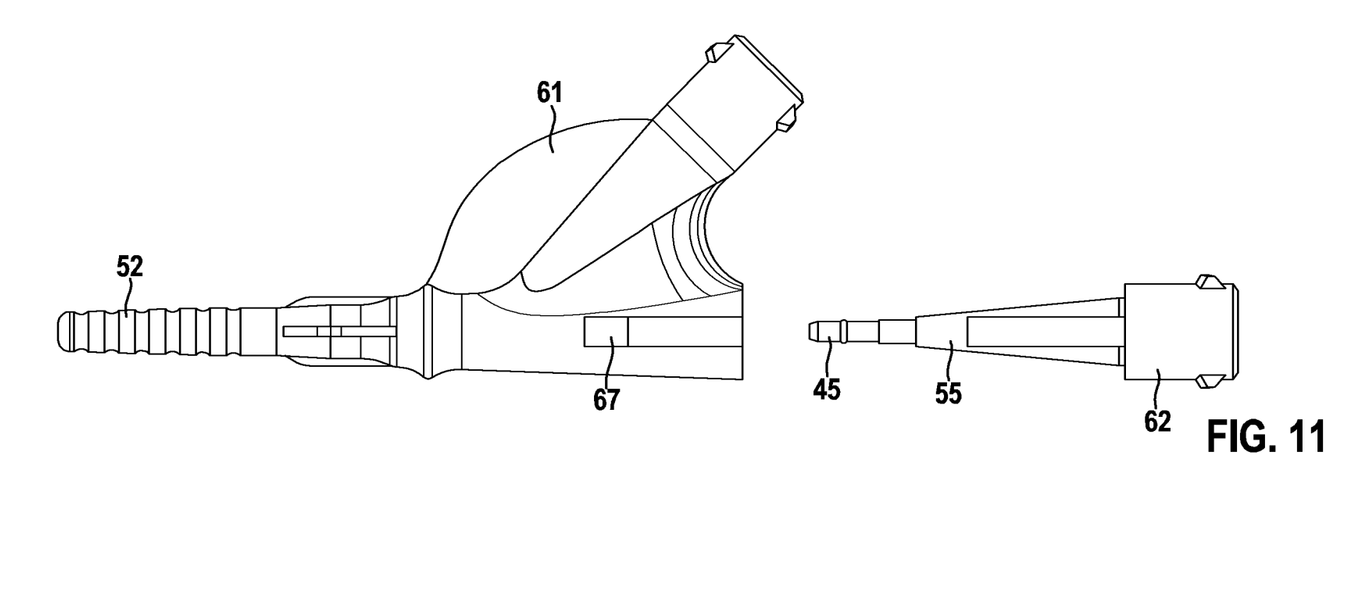
FIG. 11 shows a view from the side of another separated illustration of the distal element and the proximal element of the embodiment according to FIG. 8.
Figure 12:
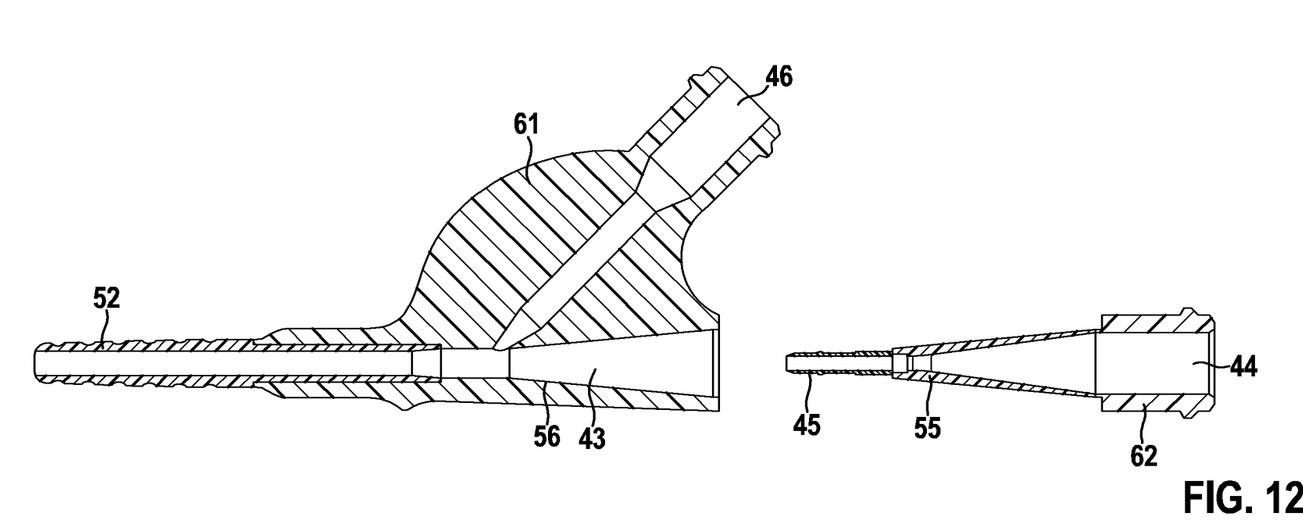
FIG. 12 shows a cross section of another separated illustration of the distal element and the proximal element of the embodiment according to FIG. 8.
Figure 13:
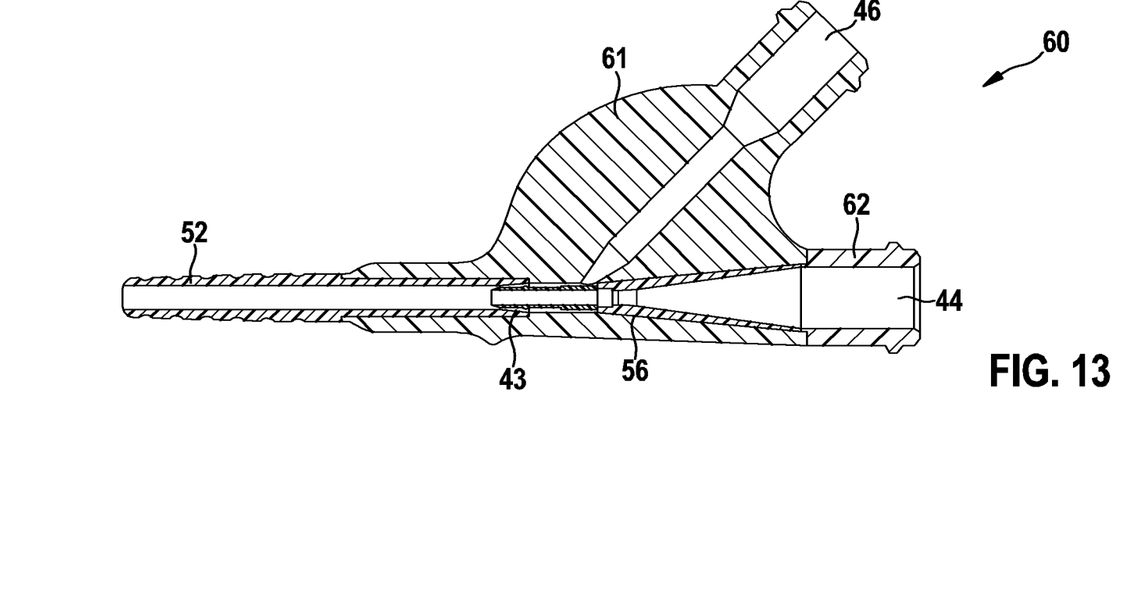
FIG. 13 shows another cross section of the embodiment of a connecting piece according to FIG. 8.
Figure 14:
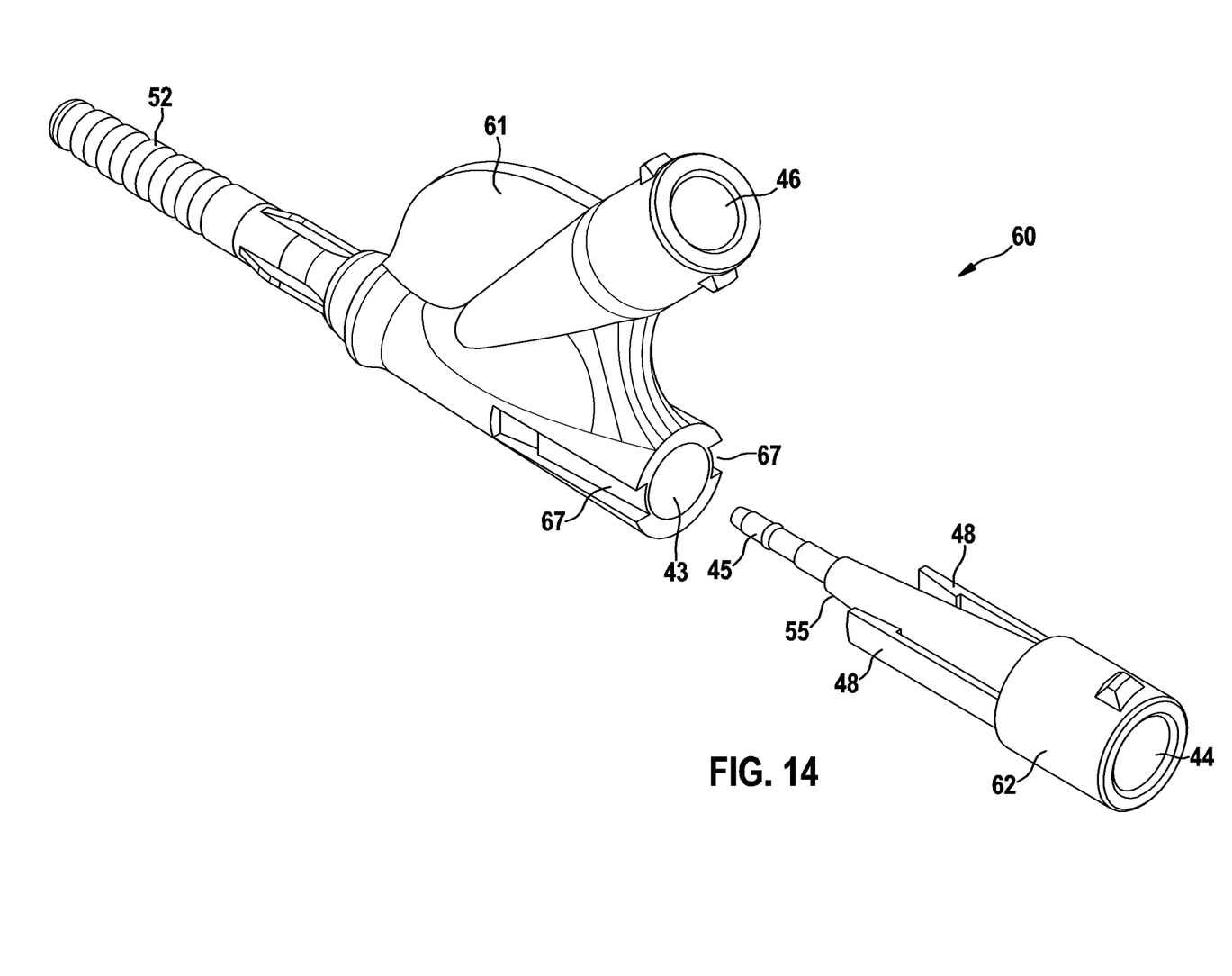
FIG. 14 shows a perspective view from the side of another separated illustration of the distal element and the proximal element of the embodiment according to FIG. 8.
Figure 15:
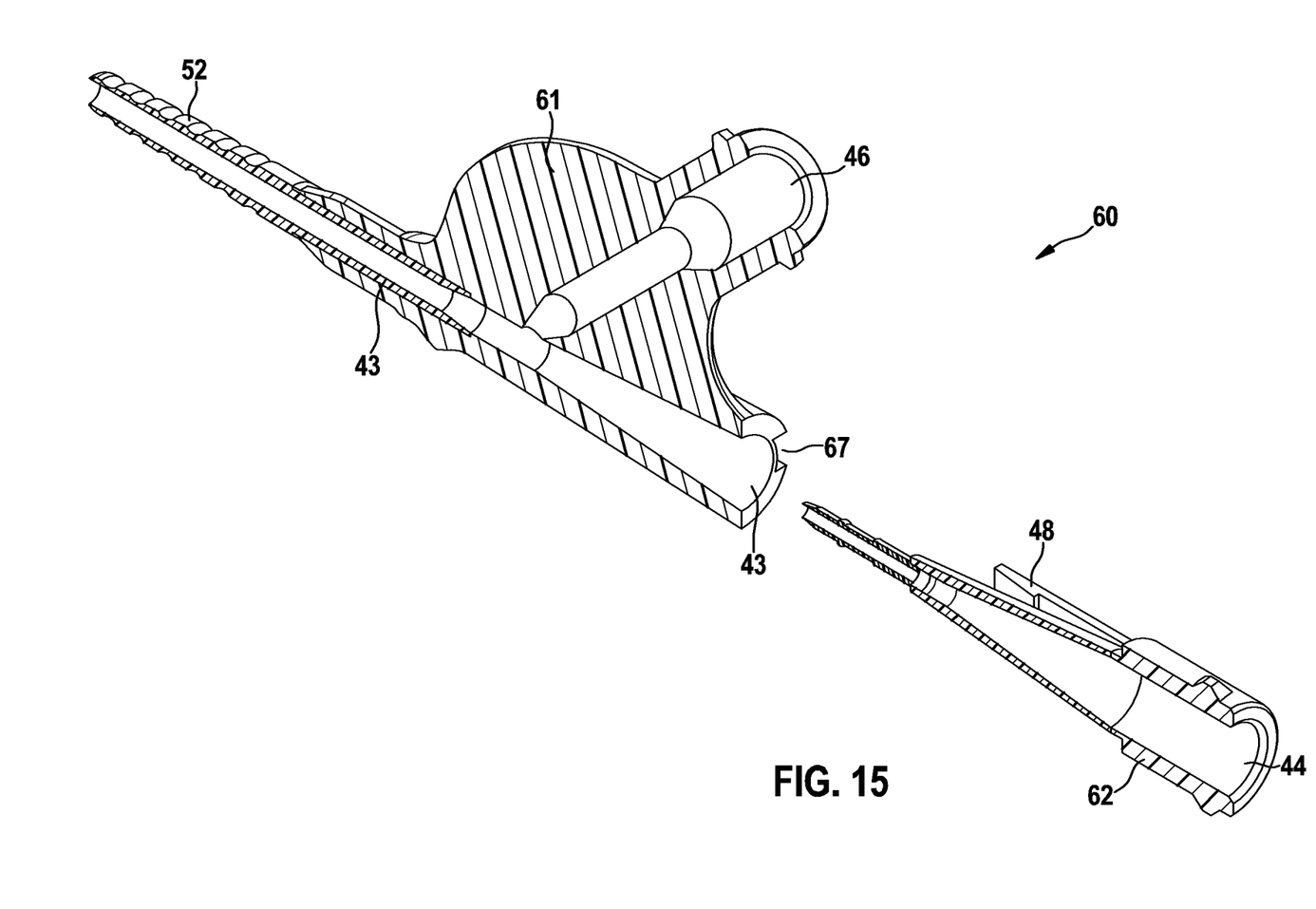
FIG. 15 shows a perspective view from the side of another separated illustration of the distal element and the proximal element of the embodiment according to FIG. 8.

The catheter according to the embodiment shown in FIG. 3B is very similar to the embodiment as shown in FIG. 3A. The connecting piece 20 includes some reinforcement 28. This embodiment is particularly advantageous for catheters employing small sized balloons (3-5 mm), which usually work at higher pressure ranges. The reinforcement 28 ensures fluid tightness of the connecting piece 20.

After the proximal end of the catheter shaft 10 has been completely inserted into the connecting piece 20, the outer surface of the first tube 11 and the outer surface of the second tube 12 are bonded, in the region of the distal end 21 of the body of the connecting piece 20, to the inner surface of the connecting piece by adhesive 27, thereby preventing the first tube 11 from sliding off of the conical section 25.

FIGS. 4 to 7 show a second embodiment of a connecting piece 40 for a catheter according to the invention, which has a two-piece design having a distal element 41 and a proximal element 42. Both elements 41, 42 are substantially hollow-cylindrical.

The distal element 41 has a continuous opening 43, into which the proximal end of the catheter shaft can be inserted. Correspondingly, the proximal element 42 has a continuous opening 44 for the placement of the guide wire. A first conical section is provided on the distal end 45 thereof, on the outer side (jacket) of the proximal element 42. In addition, the distal element 41 provides a diagonally extending channel 46 for connection to a fluid source for the inflation/deflation of a non-illustrated balloon, which is connected at the catheter shaft. The channel 46 extends into the continuous opening 43 of the distal element 41.

The distal element 41 also has, at the proximal end thereof, a slot-shaped blind hole 47 having an undercut for the placement of a web 48, which protrudes from the proximal element 42 in the distal direction and which has a hook-shaped thickening on the distal end thereof. In addition, a guide groove 49 having a rounded cross section is provided at the proximal end of the distal element 41, which cooperates with a correspondingly shaped web 50 at the distal end of the proximal element 42 when the distal element 41 is joined with the proximal element 42.

The distal element 41 furthermore includes an anti-kink element 52 at the distal end thereof, which is composed of adjacently disposed annular elements, which are connected by webs extending in the longitudinal direction.

In addition, a second conical section 55 is provided on the proximal element 42 in a central region relative to the extension of the element in the longitudinal direction. Correspondingly, the distal element also has a conical section 56 on the proximal end thereof, in the region of the inner wall.

In order to produce the catheter according to the invention by the above-described catheter shaft and the connecting piece 40 illustrated in FIGS. 4 to 7, the proximal end of the catheter shaft is first inserted into the continuous opening 43 of the distal element 41. The insertion can be supported by the guide wire. The annular elements and webs of the anti-kink element 52 are then arranged on the outer side of the first tube 11.

Next, the proximal element 42 is inserted into the inner lumen of the second tube 12 to the extent that the second conical section 55 of the proximal element 42 protrudes from the second tube. By contrast, the first conical section at the distal end 45 of the proximal element 62 is arranged in the second tube 12.

The distal element 41 is then displaced in the proximal direction on the catheter shaft in the direction of the proximal element 42, wherein the web 48 is inserted into the blind hole 47 and the web 50 is inserted into the groove 49. At the end of the displacement path, the hook-shaped thickening of the web 48 engages behind the undercut of the blind hole 47 and thereby fastens the proximal element 42 on the distal element 41 in the form of a snap-in connection. The second tube 12 is simultaneously sealed by the first conical section of the distal end 45 of the proximal element 62. In addition, a form-fit connection between the second conical section 55 of the proximal element 42 and the conical section 56 of the distal element 41 brings about a sealing of the inflation lumen of the first tube 11.

FIGS. 8 to 15 show a third embodiment of a connecting piece 60 for a catheter according to the invention, which has a two-piece design having a distal element 61 and a proximal element 62. Both elements 61, 62 are designed substantially similar to the second embodiment according to FIGS. 4 to 7 and are hollow-cylindrical. The reference numerals of the elements 61, 62, which correspond to those of the second embodiment, relate to the same regions of the connecting piece.

In the third embodiment of a connecting piece, a different type of fastening of the distal element 61 on the proximal element 62 takes place, namely by two webs 48, which protrude from the proximal element 62 in the distal direction and have a hook-shaped thickening on the distal end thereof, and correspondingly shaped notches (recesses) 67, which are mounted in the outer surface of the distal element 61. Every notch has an undercut, which is used to arrange the hook-shaped thickening on the distal end of the web 48. When the proximal element is fastened, a form-fit connection therefore results. The notches 67 are used to simultaneously guide the webs 48. Therefore, an additional guide web is not required in this embodiment, as is the case in the second embodiment.

In addition, the distal end 45 of the proximal element 62 has a different shape. This includes a plurality of adjacently disposed sections, which are partially conical.

Simple assembly of the catheter is achieved by the multi-piece connecting pieces 40 and 60 illustrated in FIGS. 4 to 15, which brings about a secure and fluid-tight connection between the catheter shaft and the connecting piece.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

- 10 catheter shaft
- 11 first tube
- 12 second tube
- 15 weld seam
- 20 connecting piece
- 21 distal end of the body of the connecting piece 20
- 25 conical section
- 26 channel
- 27 adhesive
- 28 reinforcement
- 40, 60 connecting piece
- 41, 61 distal element
- 42, 62 proximal element
- 43 continuous opening
- 44 continuous opening
- 45 distal end of the proximal element 42, 62
- 46 channel for inflation/deflation
- 47 blind hole
- 48 web
- 49 groove
- 50 web
- 52 anti-kink device
- 55 second conical section
- 56 conical section
- 67 notch

What is claimed is:

1. A catheter, comprising:
   a connector comprising a body;
   a longitudinal channel extending through the body;
   a diagonal channel through the body, wherein the diagonal channel comprises a diagonal channel opening fluidly connected to the longitudinal channel;
   a conical-shaped sealing element within the longitudinal channel, the conical-shaped sealing element extending distally beyond the diagonal channel, the conical-shaped sealing element defining a first lumen;
   a first tube defining an inflation lumen, wherein a proximal opening of the inflation lumen is distal of the diagonal channel opening and in fluid communication with the diagonal channel opening;
   a second tube attached and sealed to the conical-shaped sealing element, wherein a lumen of the second tube defines a continuation of the first lumen;
   a longitudinal weld seam extending from an outer surface of the second tube to an inner surface of the first tube;
   wherein the first tube and the second tube terminate proximally at a same longitudinal position;
   wherein sole access to the proximal opening of the inflation lumen is through the diagonal channel.

2. The catheter according to claim 1, wherein the longitudinal weld seam extends over an entire length of the first tube and the second tube.

3. The catheter according to claim 1, wherein the longitudinal weld seam comprises a plurality of separate weld segments spaced longitudinally over the first tube and the second tube with each neighboring weld seam segment of the plurality of separate weld segments being longer than spacing between neighboring weld seam segments.

4. The catheter according to claim 1, wherein the first tube is made of PEBAX, and the second tube is made of PA12.

5. The catheter according to claim 4, wherein the second tube is welded longitudinally to the inner surface of the first tube over an entire length of the first tube and an entire length of the second tube to form the longitudinal weld seam.

6. The catheter of claim 1, wherein the conical-shaped sealing element comprises a conical-shaped proximal section of the body.

7. The catheter of claim 1, wherein the conical-shaped sealing element comprises a conical-shaped proximal element inserted into and attached to the body.

8. The catheter according to claim 7, wherein the body and the conical-shaped proximal element comprise a snap-in connection.

9. The catheter according to claim 8, further comprising an anti-kink device on a distal end of the body, wherein the anti-kink device comprises adjacently disposed annular elements connected by webs extending in a longitudinal direction.

10. The catheter according to claim 7, wherein the conical-shaped proximal element and the body fit together by insertion of a web into a blind hole.

11. The catheter according to claim 7, wherein the conical-shaped proximal element fits into and protrudes from the continuation of the first lumen defined by the second tube.

* * * * *